United States Patent [19]
Osypka

[11] Patent Number: 5,843,154
[45] Date of Patent: Dec. 1, 1998

[54] APPARATUS FOR PERFORMING DIAGNOSTIC AND/OR THERAPEUTICAL HEART INTERVENTIONS WITH A CATHETER

[75] Inventor: Peter Osypka, Grenzach-Wyhlen, Germany

[73] Assignee: Sulzer Osypka GmbH, Grenzach-Wyhlen, Germany

[21] Appl. No.: 938,741

[22] Filed: Sep. 26, 1997

[30] Foreign Application Priority Data

Sep. 27, 1996 [EP] European Pat. Off. .............. 96810640

[51] Int. Cl.⁶ ..................................................... A61B 5/00
[52] U.S. Cl. ............................................................. 607/122
[58] Field of Search .................................. 606/41, 45, 46; 604/264, 19, 27; 600/373, 374; 607/116, 119, 122

[56] References Cited

U.S. PATENT DOCUMENTS

| 5,140,987 | 8/1992 | Schuger . |
| 5,417,669 | 5/1995 | Castaneda . |
| 5,487,385 | 1/1996 | Avitall . |
| 5,718,692 | 2/1998 | Schon et al. ............................ 604/264 |

FOREIGN PATENT DOCUMENTS

| 0659388A1 | 6/1995 | European Pat. Off. . |
| 0692221A2 | 1/1996 | European Pat. Off. . |
| 0711573A1 | 5/1996 | European Pat. Off. . |
| WO94/02077 | 2/1994 | WIPO . |

*Primary Examiner*—George Manuel
*Attorney, Agent, or Firm*—Townsend and Townsend and Crew LLP

[57] ABSTRACT

The apparatus for performing diagnostic and/or therapeutical heart interventions comprises a catheter (1) which contains a guided catheter (2), a guiding catheter (3) surrounding the guided catheter and a guide wire (4) extending within a lumen (20) of the guided catheter. Means (7) are provided which permit a controlled change of position of the guide wire in a chamber of the heart. The catheter is a first catheter (1) whose guide wire is in connection with the distal end (30') of a second catheter (1') or can be connected thereto respectively. The second catheter can be positioned in the heart in such a manner that its distal end takes on a stationary position independent of the change in position of the guide wire.

11 Claims, 2 Drawing Sheets

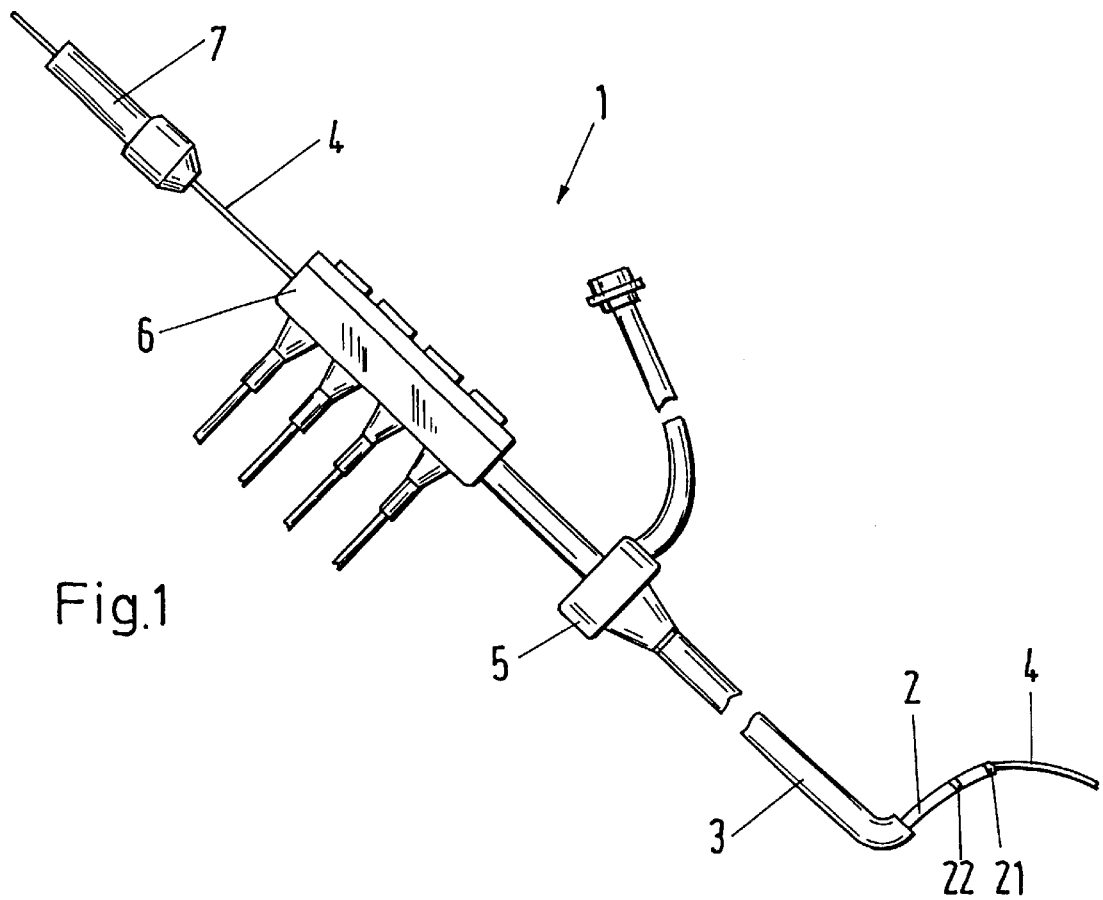
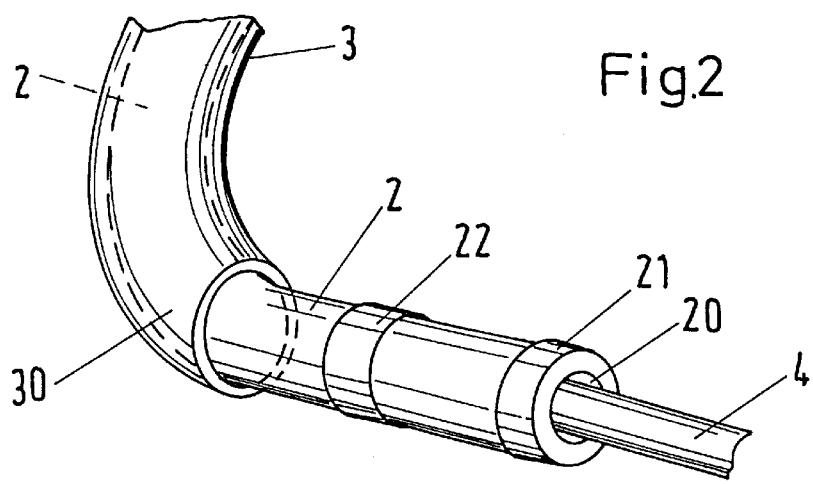

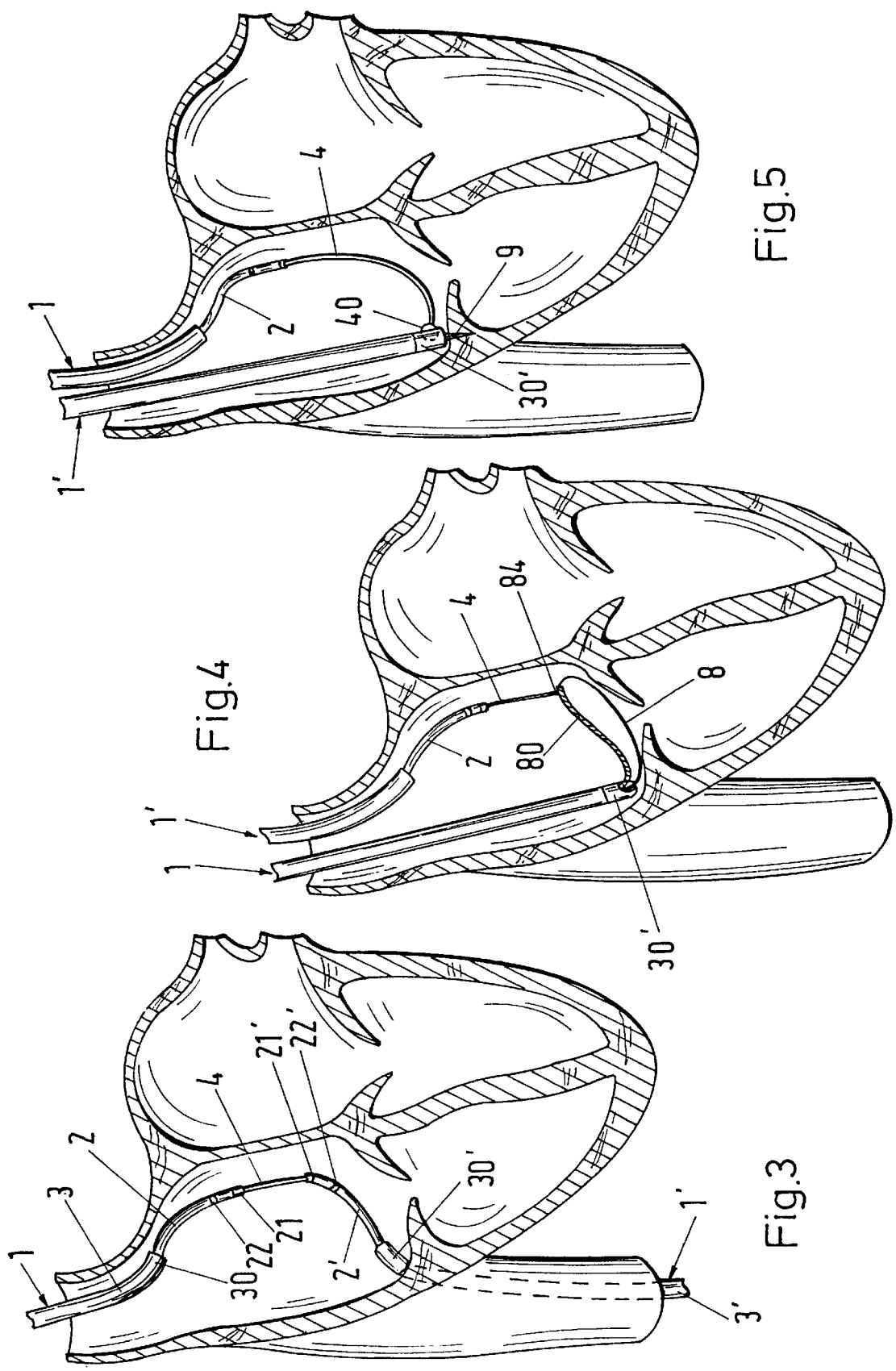

though the tension of the support loop 8 and can be moved along the wall of the heart, with the wall being treatable, e.g. by ablation, from the poles 21 of the first catheter 1.

APPARATUS FOR PERFORMING DIAGNOSTIC AND/OR THERAPEUTICAL HEART INTERVENTIONS WITH A CATHETER

The invention relates to an apparatus for performing diagnostic and/or therapeutical heart interventions with a catheter in accordance with the preamble of claim 1.

An apparatus of this kind is known from EP-A 0 692 221, namely a catheter with a guide hose and a multiple electrode. This catheter has at its distal end a support loop of bendable or flexible material which can be pushed out of the guide hose and increased or decreased in its circumference. The support loop serves in a particular embodiment (see FIG. 6 of EP-A 0 692 221) as a holder for a further guide wire which can likewise be pushed out of the guide hose. By rotating and pushing the guide wire, the latter can be brought into contact with the inner wall in a chamber of the heart by following the wall contours. The multiple electrode provided is a multiple spiral in whose inner channel the guide wire extends. The inner wall of the heart can be probed by a controlled change of the position of the guide wire and a displacement of the multiple electrode along the guide wire. With an apparatus of this kind the wall is treated strip by strip, with a predetermined respective positioning of the guide wire being associated with each strip. As a result of the pumping movement of the heart, problems can arise in regard to a stable positioning of the guide wire.

The object of the invention is to provide an apparatus of this kind by means of which the named strip-wise treatment can be performed with a guide wire which is stably positioned in each case—even in the presence of particularly smooth places on the inner wall of the heart.

This object is satisfied by an apparatus with the features of claim 1. This apparatus for performing diagnostic and/or therapeutical heart interventions has a catheter which comprises a guided catheter, a guide catheter surrounding the guided catheter and a guide wire extending within a lumen of the guided catheter. Means are provided which permit a controlled change of position of the guide wire in a chamber of the heart. The catheter is a first catheter whose guide wire is in connection with the distal end of a second catheter or can be connected to the latter respectively. The second catheter can be positioned in the heart in such a manner that its distal end adopts a stationary position independent of the change in the position of the guide wire.

One obtains a good stability of the guide wire by the use, in accordance with the invention, of a guide wire which is arranged between the distal ends of two catheters and is also movable between these ends, because the distal ends of the catheter can be positioned within the heart or at the entrance to the heart in such a manner that they take on stationary positions in spite of the movement of the heart. These stationary positions represent fixed predetermined boundary conditions for the guide wire which impart the required stability to the movable wire. The guide wire can be manipulated from both ends in the apparatus in accordance with the invention by rotation and pushing.

The dependent claims 2 to 11 relate to diverse embodiments of the method in accordance with the invention.

The invention will be explained in the following with reference to the drawings. Shown are:

FIG. 1 a catheter which forms a part of the apparatus in accordance with the invention, FIG. 2 a detail of the catheter shown in FIG. 1, FIG. 3 the parts of a first embodiment of the apparatus in accordance with the invention which is introduced into the heart, FIG. 4 an illustration corresponding to FIG. 3 for a second embodiment and FIG. 5 the illustration of a third embodiment.

The catheter 1 shown in FIG. 1 comprises the following components: a guided catheter 2—executed here as an electrode catheter with poles 21 and 22; a guide catheter 3 with a distal end 30; a guide wire 4; a lock or antechamber; an electrode connection; furthermore a handle for the proximal end of the guide wire 4.

The perspective view of FIG. 2 shows the distal end 30 of the guiding catheter 3 illustrated in FIG. 1. At the distal end of the guided catheter 2 an inner channel or lumen 20 can also be seen in which the guide wire 4 extends.

The guide wire 4 is advantageously preformed in accordance with the anatomy of the heart. The material Nitinol is especially suitable for this preforming. Instead of Nitinol other bendable or flexible materials of metallic alloys or even polymers can be considered.

The second catheter 1' of the embodiment of the invention shown in FIG. 3 comprises a second guided catheter 2', and the two catheters 1 and 1' have a common guide wire 4.

The second catheter 1' can be introduced into the heart independently of the first catheter 1. The first catheter 1 enters into the heart via a first blood vessel, namely via the vena subclavia; the second catheter 1' via a second blood vessel, namely the vena femoralis. When pushing the second catheter 1' into the vena femoralis—not illustrated—the former contains a capture member, for example a capture catheter with a loop by means of which a bent tip of the guide wire 4 of the first catheter 1 can be grasped. The guide wire 4 is drawn into the second catheter 1' by means of the capture member. The catheter 1 with the antechamber or lock 5 (see FIG. 1) as well as the catheter 1' can be introduced into the body of the patient using the known Seldinger technique.

Plastic handles 7 (see FIG. 1), which can be attached to the two ends of the guide wire 4 after the insertion, facilitate the manipulation (turning, pushing, pulling) of the wire 4.

The guided catheters 2 and 2' are executed as electrode catheters. Heart potentials can be sensed (so-called "mapping") with their poles 21, 22, 21' and 22' and/or high frequency current can be applied by them for the ablation of tissue. Temperature sensors in particular are also arranged at the poles serving for ablation (not illustrated) and are provided for the regulation of the high frequency current to avoid an overheating of the tissue to be treated.

The distal ends 30, 30' of the two guide catheters 3, 3' are positioned directly at the entrances to the right auricle of the heart. With these positionings a stable position results for the common guide wire 4 which is not disturbed by the movements of the heart.

In the embodiments of FIGS. 4 and 5 the introductions of the catheters into the heart are provided in such a way that they enter into the heart via the same blood vessel, namely the vena subclavia.

In the example of FIG. 4 the distal end 30' of the second catheter 1' is provided with a flexible support loop 8 for fixing the catheter 1' in the heart; this loop is executed so that it can be pushed out. The loop 8 serves, on the one hand, for fixing the catheter 1' at an arbitrary position in the heart. On the other hand, the distal end of the guide wire 4 is positioned on the loop, and indeed with a metal spiral 80 which is pushed over the loop and at whose end 84 the guide wire 4 is fastened (cf. FIG. 4 in EP-A 0 692 221). By pulling and pushing the spiral 80, the guide wire 4 can be positioned within the heart practically over the entire extent of 360°. The wire 4 is pressed against the wall of the heart through the guidance via the first catheter 1. The actual mapping and ablation electrode 2 is pushed via the guide wire 4—see the exemplary embodiment (FIG. 3).

In the exemplary embodiment of FIG. 5 the distal end 30' of the second catheter 1' is provided with a tip 9 for fixing the catheter 1' in the heart; it is designed to be extensible. The guide wire 4 of the first catheter 1 is connected to the distal end 30' of the second catheter 1' via a joint 40.

In the embodiments of the apparatus in accordance with the invention shown in FIGS. 3 to 5 the guided catheters 2 are executed in each case as mapping and ablation electrodes. It is however also possible that the guided catheters 2 contain light conducting fibres. With the use of such fibres a visual diagnosis or a check on the treatment steps can be carried out and/or laser beam energy can be introduced into the heart for the treatment of tissue.

The term intervention used in this application will be understood to mean a surgical operation or intervention, or an invasive action associated with treatment or diagnosis.

I claim:

1. Apparatus for performing diagnostic and/or therapeutical heart interventions with a catheter (1) which comprises a guided catheter (2), a guiding catheter (3) surrounding the guided catheter and a guide wire (4) extending within a lumen (20) of the guided catheter, with means (7) being provided which permit a controlled change of position of the guide wire in a chamber of the heart, characterised in that the catheter is a first catheter (1) whose guide wire is in connection with the distal end (30') of a second catheter (1') or can be connected thereto respectively; and in that the second catheter can be positioned in the heart in such a manner that its distal end adopts a stationary position independent of the change in position of the guide wire.

2. Apparatus in accordance with claim 1 characterised in that the second catheter (1') can be introduced into the heart independently of the first catheter (1).

3. Apparatus in accordance with claim 2 characterised in that the second catheter (1') comprises a capture member by means of which the guide wire (4) of the first catheter (1) can be grasped and pulled into the second catheter.

4. Apparatus in accordance with claim 3 characterised in that the second catheter (1') comprises a second guided catheter (2'); and in that the first catheter (1') and the second catheter have a common guide wire (4).

5. Apparatus in accordance with claim 4 characterised in that handles (7) are provided for the common guide wire (4), which handles can be attached to the two ends of the guide wire once it has been drawn in and facilitate the manipulation for the controlled change of the position of the wire.

6. Apparatus in accordance with claim 1 characterised in that the introductions of the catheters (1, 1') into the heart are carried out in such a manner that the first catheter (1) enters the heart via a first blood vessel, in particular the vena subclavia, and the second catheter (1') via a second blood vessel, in particular the vena femoralis.

7. Apparatus in accordance with claim 1 characterised in that the introductions of the catheters (1, 1') into the heart are provided in such a manner that they enter the heart via the same blood vessel, in particular the vena subclavia.

8. Apparatus in accordance with claim 1 characterised in that the distal end (30') of the second catheter (1') contains a flexible support loop (8) which is provided for fixing the catheter in the heart and which is formed so that it can be thrust outwards.

9. Apparatus in accordance with claim 1 characterised in that the distal end (30') of the second catheter (1') contains a tip (9) which is provided for fixing the catheter in the heart and which is formed to be movable outwards.

10. Apparatus in accordance with claim 1 characterised in that the guided catheter or catheters (2, 2') are executed as electrode catheter(s) by means of whose poles (21, 22, 21', 22') heart potentials can be picked up and/or high frequency current can be applied for the ablation of tissue, with temperature sensors in particular being arranged at the poles for the ablation and being provided for a regulation of the high frequency current in order to avoid an overheating of the tissue to be treated.

11. Apparatus in accordance with claim 1 characterised in that the guided catheter or catheters (2, 2') contain light conducting fibres by means of which a visual diagnosis or a checking of treatment steps is possible and/or by means of which light energy, in particular laser radiation, can be introduced into the heart for the treatment of tissue.

* * * * *